(12) United States Patent
Jiang et al.

(10) Patent No.: US 8,920,323 B2
(45) Date of Patent: Dec. 30, 2014

(54) COUPLED AXIAL AND LATERAL DISPLACEMENT ESTIMATION FOR ELASTICITY IMAGING

(75) Inventors: Jingfeng Jiang, Madison, WI (US); Timothy J. Hall, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 726 days.

(21) Appl. No.: 12/903,748

(22) Filed: Oct. 13, 2010

(65) Prior Publication Data

US 2012/0095333 A1 Apr. 19, 2012

(51) Int. Cl.
*A61B 8/00* (2006.01)
*A61B 8/08* (2006.01)
*A61B 5/00* (2006.01)
*G01S 15/89* (2006.01)
*G01S 7/52* (2006.01)

(52) U.S. Cl.
CPC .............. *A61B 8/485* (2013.01); *A61B 5/0053* (2013.01); *A61B 8/5207* (2013.01); *G01S 15/8993* (2013.01); *G01S 7/52042* (2013.01)
USPC .......................... 600/438; 600/437; 600/443

(58) Field of Classification Search
None
See application file for complete search history.

(56) References Cited

U.S. PATENT DOCUMENTS

| 6,508,768 | B1 | 1/2003 | Hall et al. | |
|---|---|---|---|---|
| 2004/0208341 | A1* | 10/2004 | Zhou et al. | 382/103 |
| 2005/0165309 | A1* | 7/2005 | Varghese et al. | 600/449 |
| 2007/0234806 | A1* | 10/2007 | Jiang et al. | 73/570 |
| 2010/0106018 | A1 | 4/2010 | Jiang et al. | |

OTHER PUBLICATIONS

Jiang et al. "A generalized speckle tracking algorithm for ultrasonic strain imaging using dynamic processing", NIH Public Access, Published Online Aug. 2009, pp. 1-18.*
Leibgott et al., "PSF dedicated to estimation of displacement vectors for tissue elasticity imaging with ultrasound", IEEE Transactions of Ultrasonics, vol. 54, No. 4, Apr. 2007.*
Ebbini, Emad S., Phase-Coupled Two-Dimensional Speckle Tracking Algorithm, vol. 53, No. 5, May 2006, pp. 972-990, IEEE Transactions on Ultrasonics, Ferroeletrics, and Frequency Control, IEEE, New York, NY, USA.
Samani, Abbas, et al., A Method to Measure the Hyperelastic Parameters of Ex Vivo Breast Tissue Samples, Physics in Medicine and Biology, 49 (2004) pp. 4395-4405, IOP Publishing, Ltd., Bristol, UK.
Wellman, Parris S., Breast Tissue Stiffness in Compression is Correlated to Histological Diagnosis, Technical Report, Harvard Biorobotics Laboratory, 1999, Cambridge, MA, USA.
Oberai, Assad, Linear and nonlinear elasticity imaging of soft tissue in vivo: demonstration of feasibility, Physics in Medicine and Biology, 54 (2009) pp. 1191-1207, IOP Publishing, Ltd., Bristol, UK.

* cited by examiner

*Primary Examiner* — Christopher Cook
(74) *Attorney, Agent, or Firm* — Boyle Fredrickson, S.C.

(57) ABSTRACT

The determination of axial and lateral displacement in a material subject to compression is determined by fitting a multi-dimensional model function to the match between corresponding portions of the material in two states of compression. In one embodiment, iso-contour lines in a correlation between a reference kernel and a target kernel are fit to an ellipse whose center defines the maximum correlation and hence the displacement.

18 Claims, 2 Drawing Sheets

COUPLED AXIAL AND LATERAL DISPLACEMENT ESTIMATION FOR ELASTICITY IMAGING

STATEMENT REGARDING FEDERALLY SPONSORED RESEARCH OR DEVELOPMENT

This invention was made with government support under CA100373 and CA140271 awarded by the National Institutes of Health. The government has certain rights in the invention.

CROSS-REFERENCE TO RELATED APPLICATIONS

N/A

BACKGROUND OF THE INVENTION

The present invention relates to elasticity imaging including but not limited to strain imaging and in particular to an improved method of determining displacement vectors used to produce such images.

Strain imaging produces images revealing the underlying elastic parameters of the material being measured. When used in medicine, strain imaging is analogous to palpation by a physician, that is, the pressing of tissue by the physician to feel differences in elasticity in the underlying structures.

In a common form of strain imaging, two separate images are obtained with the measured material in different states of deformation, typically, as deformed by a mechanical or physiological stimulus. In ultrasound strain imaging, the ultrasound probe itself may be used to provide this deformation.

The two images are analyzed to deduce the amount of displacement in the material at a number of corresponding regions. The gradient in these displacements, determined as a function of the spatial location of the regions, provides strain information generally reflecting the elasticity of the tissue. An example of such strain imaging and a description of techniques for determining displacement of tissue between two images are described in detail in U.S. Pat. No. 6,508,768 entitled: Ultrasonic Elasticity Imaging, and in pending U.S. application Ser. No. 12/258,532 filed Oct. 27, 2008 and entitled: Ultrasonic Strain Imaging Device with Selectable Cost-Function, and in pending U.S. application Ser. No. 12/645,936 filed Dec. 23, 2009 and entitled: Elasticity Imaging Device with Improved Characterization of Seed Displacement Calculations, all assigned to the same assignee as the present invention and hereby incorporated by reference.

The displacement between corresponding regions of the material in the first and second state of deformation can be determined by identifying a multi-point region (i.e. a reference kernel) in the material in the first state of deformation and moving this kernel within a two- or three-dimensional search region over a search region of the material in the second state of deformation. The displacement vector is determined by the best match between the reference kernel and its overlapping portion in the search region of the material in the second state of deformation (i.e. the target kernel). The best match may be determined by evaluating a similarity of the data of the reference and target kernels, for example, as a sum of the magnitude of differences between individual samples of these two kernels or other similar technique.

In ultrasonic imaging systems, the determination of displacement may be limited to an axial direction defined by the propagation of the ultrasonic signal. This is because motion tracking in the lateral direction (perpendicular to the axial direction) tends to be of low quality possibly because of the loss of phase information because sequential data in the lateral direction is assembled from multiple rather than a single beam.

Nevertheless lateral displacement information can be valuable because it provides a more complete picture of elasticity necessary for many types of measurement.

SUMMARY OF THE INVENTION

The present invention provides a method of improved lateral displacement determination in elasticity imaging by using a coupled determination of axial and lateral displacement that informs the determination of each axis of displacement with the other. In one embodiment, a multi-dimensional model function is fit to a comparably dimensioned map of correlation between the reference kernel and the target kernel and displacement is derived from the location of the fit model function. This fitting process beneficially combines the determination of axial and lateral displacement.

Specifically, the present invention provides in one embodiment, an apparatus for obtaining elasticity images indicating elastic properties of a material subject to periodic compression. The apparatus may include an imaging device for obtaining reference and target image information at different compressions, the image information having at least two spatial dimensions. An electronic computer that may be shared with the imaging device executes a stored program and receives the image information to compare corresponding portions of the reference and target image information. This comparison produces, for each compared portion, match-quality information indicating a matching between the corresponding portions at multiple points in at least two spatial dimensions. A match-model having at least two spatial dimensions is then fit to the match-quality information for each compared portion and a displacement value for at least one of the compared portions is extracted from the fit match model. Optionally, a human readable output is provided based on the multiple extracted displacement values.

It is thus a feature of at least one embodiment of the invention to provide a simultaneous fitting of axial and non-axial data to improve non-axial estimates of displacement and strain.

The match-model may be a Gaussian function representing expected matching in an elastic material.

It is thus a feature of at least one embodiment of the invention to employ a match model derived from the point spread function of a typical imaging machine.

The match-quality information and the match-model may have at least two spatial dimensions. In two spatial dimensions, the match-model is an ellipse fit to a contour line of the match-quality information following a line of constant match-quality, while in three dimension, such a model may be an ellipsoid fit to a contour surface of the match-quality information following a surface of constant match-quality.

It is thus a feature of at least one embodiment of the invention to provide a system applicable to at least two-dimensional image information.

The constant match-quality may be determined from the peak match-quality.

It is thus a feature of at least one embodiment of the invention to select a contour line or contour surface that best uses the obtainable signal, making a trade-off between a number of data points in the contour line and signal-to-noise ratio of the data of the contour line or contour surface.

The imaging apparatus may be an ultrasound machine collecting data along an axis by electronically manipulating received ultrasound data along the direction of acoustic waves, and wherein the three spatial dimensions are one aligned with the axis and the other two perpendicular to the axis.

It is thus a feature of at least one embodiment of the invention to provide a method of augmenting the lower resolution inherent in the non-axial dimensions of an ultrasound machine for improved displacement measurement.

The output may be images of at least one of displacement and strain related quantity.

It is thus a feature of at least one embodiment of the invention to provide improved elastographic images.

The electronic computer may select the portions of the reference and target image information for the comparison using pattern matching of the reference and target regions.

It is thus a feature of at least one embodiment of the invention to combine the rapid computational benefits of pattern matching with the present invention.

The electronic computer may up sample the portions before the comparison.

It is thus a feature released one embodiment of the invention to increase points of comparison for the matching process.

These particular objects and advantages may apply to only some embodiments falling within the claims, and thus do not define the scope of the invention.

BRIEF DESCRIPTION OF THE DRAWINGS

FIG. 3 is a perspective representation of the fitting of a three-dimensional model to three-dimensional match-quality data.

DETAILED DESCRIPTION OF THE PREFERRED EMBODIMENT

Figure 1:
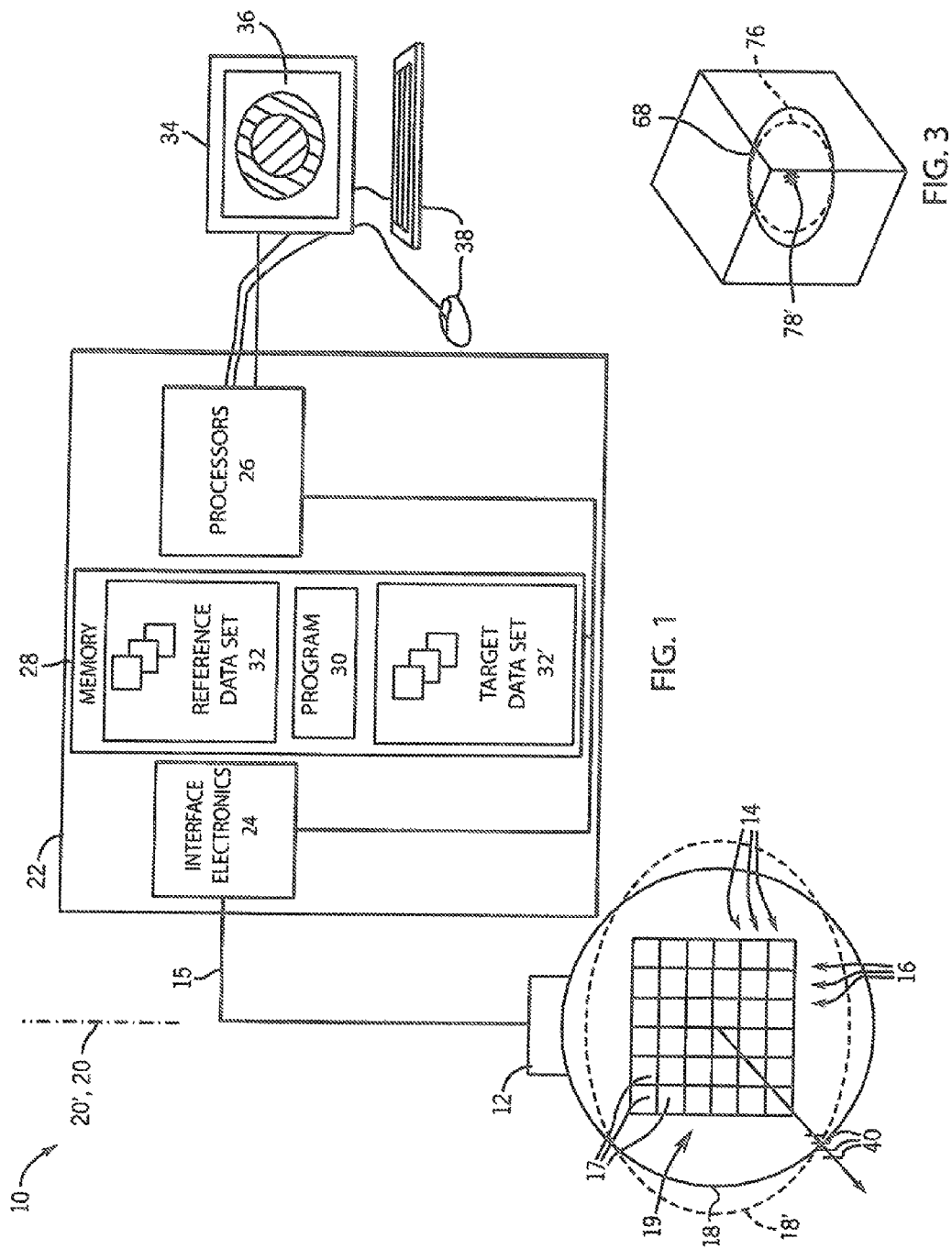
FIG. 1 is a simplified block diagram of an ultrasound machine holding a stored program suitable for execution of the present invention.

Referring now to FIG. 1, an elasticity imaging machine 10 per the present invention may include an ultrasonic array transducer 12 that may transmit and receive ultrasonic signals along a propagation axis 20 to acquire ultrasonic echo data 15 at corresponding volume elements 17 throughout a region of interest 19 in the tissue 18.

The echo data 15, and its corresponding volume elements 17, may be identified by logical rows 14, columns 16 and planes 40, wherein the rows 14 are generally different times in the echo data 15 distinguishing volume elements 17 extending perpendicularly to the propagation axis 20, and the columns 16 and planes 40 are generally different rays of the echo data 15 distinguishing volume elements 17 extending parallel to the propagation axis 20 (for the columns) or volume elements 17 extending perpendicularly to the rows 14 and columns 16 (for the planes). These terms should be understood generally to describe data acquired through a variety of acquisition geometries including those which provide for fan beams of ultrasound and the like, and should not be limited to rectilinear rows, columns and planes.

In addition to transmitting and receiving ultrasonic signals along the propagation axis 20, the transducer 12 may also provide an instrument to provide deformation along deformation axis 20' generally aligned with a propagation axis 20 of ultrasound from the transducer 12. This can be done by varying a downward pressure of the transducer 12 against the tissue 18. Generally, echo data 15 will be obtained with the tissue 18 in a first state of deformation with respect to a second state of deformation (indicated by tissue 18'), to provide pre-deformation and post-deformation tissue 18 measurements. It will be understood that characterizations of "pre-deformation" and "post-deformation" are arbitrary and in fact the pre-deformation tissue may be the tissue that is more deformed by the transducer 12. The introduction of mechanical stimuli in elasticity imaging is generally understood in the art, and is not be limited to deformation induced by transducer 12 but may include other external or internal compression systems and/or the exploitation of physiological compression mechanisms such as cardiac or resperatory mechanisms.

The transducer 12 communicates with a processing unit 22 that both provides waveform data to the transducer 12 used to control the ultrasonic beam and collects the ultrasonic echo signals (radio-frequency data) that form the echo data 15. As is understood in the art, processing unit 22 provides for necessary interface electronics 24 that may sample the ultrasonic echo signals to produce computer readable echo data 15. The interface electronics 24 may operate under the control of one or more processors 26 communicating with a memory 28, the latter which may store the echo data 15 identified to rows 14, columns 16, and optionally planes 40, to form pre-deformation "reference" data sets 32 of echo data 15 and post-deformation "target" data sets 32' as will be described further below.

As will be appreciated by those of ordinary skill in the art, reference data set 32 and target data set 32' are generally two- or three-dimensional images that include "speckles" being image characteristics associated with underlying small-scale features to the tissue 18 and 18' that can be used to deduce the displacement of the tissue 18, 18' between states of deformation.

Generally, the processors 26 may execute a stored program 30 contained in memory 28 as will also be described below. The processors 26 also may communicate with an output screen 34 on which may be displayed a strain or elasticity image 36 and with a keyboard or other input device 38 for controlling the processing unit 22 and allowing for user input as will be understood to those of skill in the art.

Figure 2:
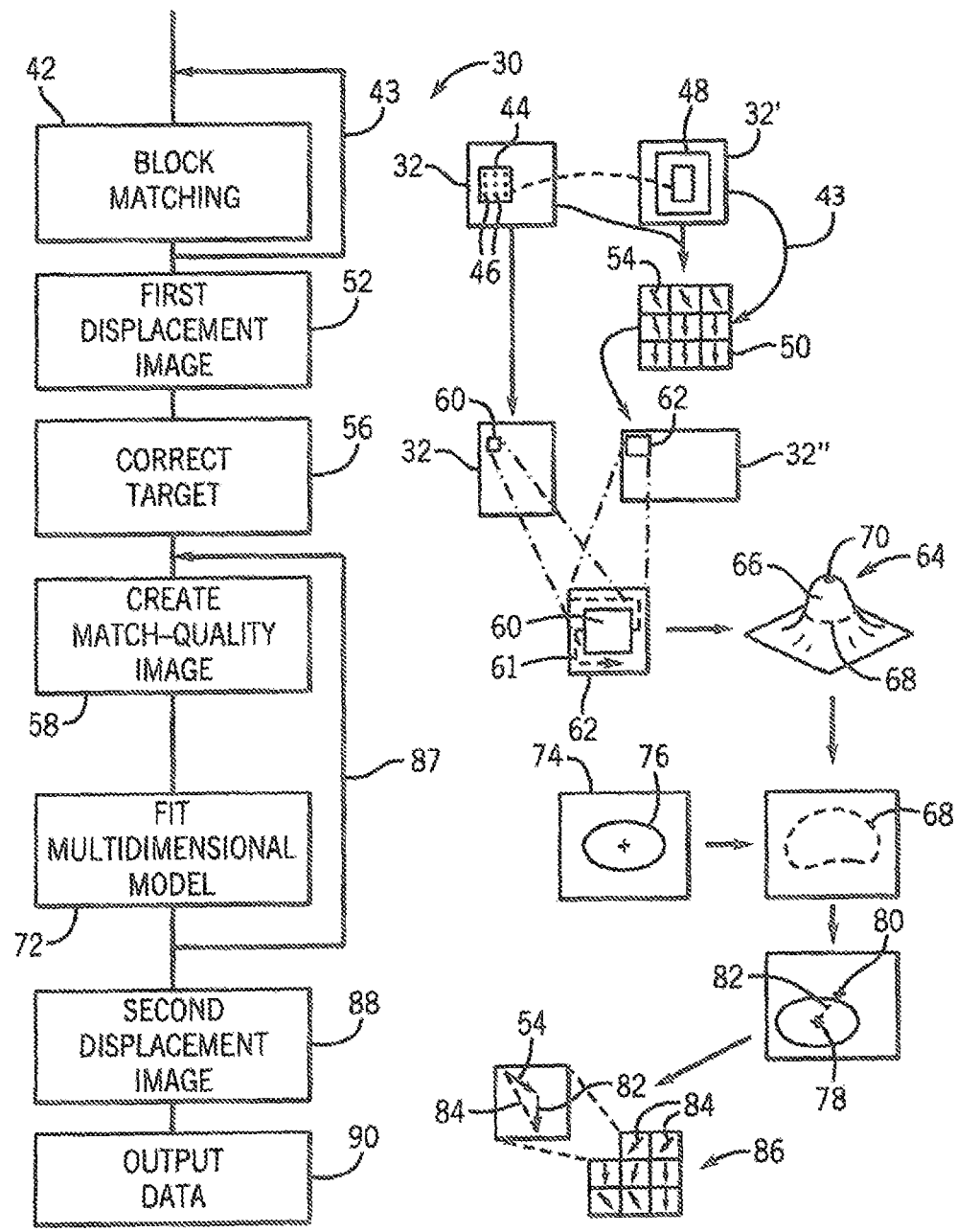
FIG. 2 is a combination flowchart and data diagram illustrating the operation of the stored program of FIG. 1.

Referring now to FIG. 2, the program 30 executed by the processors 26 may first perform a pattern matching, as indicated by process block 42, between the reference data set 32 and the target data set 32'. Such a pattern matching may be a so called block matching of a type generally understood in the art in which the reference data set 32 and target data set 32' are compared in a series of sequential blocks. In this process, a reference kernel 44 is identified in the reference data set 32 comprising a collection of adjacent data points 46 being sample points of the underlying ultrasonic signal. This reference kernel 44 is compared to data within a search window 48 in the target data set 32', for example, by sliding the reference kernel 44 through the area of the search window 48 to find the best match. The best match may be indicated, for example, by the highest correlation and defines a displacement of the data points 46 from the reference data set 32 and target data set 32' and may be expressed as a two- or three-dimensional vector.

The block matching may employ a cost function, for example, of the type described in the above referenced U.S. patent application Ser. No. 12/645,936. In particular, a cost function may be of the form of:

$$\text{COST} = \int\int_{path} (\alpha E_C + \phi E_S) dpath \qquad (1)$$

where $\alpha$ and $\phi$ are empirically selected scale factors, $E_C$ is a measure of similarity in the speckle of the regions and $E_S$ is a measure of continuity (de-correlation and motion continuity, respectively) and path is a small neighborhood at the point of displacement. In one embodiment, $E_C$ is set to 1−NCC, where NCC is the normalized cross-correlation coefficient (of the kernel 44 centered at one of candidate location within the search window 48) and $\alpha$ is set to 1.

The block matching is repeated for multiple kernels 44 (as indicated by an arrow 43) together covering the data of the reference data set 32 to produce a first displacement image 50 per process block 52. The displacement image 50 may be limited to integer portion of displacement values (because the fraction portion of integer displacement of the kernel 44 in scanning the window is less accurate). This displacement image provides a set of displacement vectors 54 for each kernel 44 and generally at regular locations over the entire area of the reference data set 32 or corresponding target data set 32′ indicating the shift necessary in each kernel 44 in the reference data set 32 necessary to produce the highest correlation in a corresponding window 48 of the target data set 32′.

Per process block 56, the displacement image 50 may optionally then be used to warp the target data set 32′ to compensate for the relative distortion caused by the measured displacement and representing the deformation, for example, imposed by compression of the transducer 12. This warping produces a corrected target data set 32″ that roughly matches the reference data set 32 in terms of the relative separation and position of data points 46 in each data set. The warping may assume local incompressibility of the tissue 18 and thus for a given axial compressive strain $\epsilon$ may provide an axial stretching and lateral compression by the amounts of $\epsilon$ and $0.5\epsilon$ respectively. The warping may use an interpolation, for example, using a fast B-spline algorithm of the type described in M. Unser, "Fast B-spline Transforms for Continuous Image Representation and Interpolation," IEEE Transactions on Pattern Analysis and Machine Intelligence, vol. 13, pp. 277-285, 1991 hereby incorporated by reference.

As indicated by process block 58, the program 30 then analyzes a set of reference kernels 60 regularly spaced in the reference data set 32 with respect to corresponding windows 62 centered about the anticipated point of highest correlation determined by the displacement vector 54 of the displacement image 50. Each reference kernel 60 is scanned in a pattern 61 with respect to the windows 62 and at each scanning point, a match-quality (for example, a correlation) is determined to create a match-quality image 64 generally either equal to or smaller than the area of the search window 48. The match-quality image 64 provides a surface 66 indicating a degree of correlation at each scanning point in the windows 62 when the reference kernel 60 is centered on that point. The reference kernel 60 and windows 62 may be up-sampled prior to this comparison process.

Theoretically, the surface 66 will be a two-dimensional Gaussian function (for two-dimensional reference data set 32) or a three-dimensional Gaussian function (for a three-dimensional reference data set 32) being a function closely related to the inherent point spread function in the imaging system. The particular aspect ratio (height to width, or height to width and depth) will depend on the fundamental bandwidth or resolution of the elasticity imaging machine 10 in the different axes of the columns, rows (and optionally planes) and compression parameters in those directions.

For each match-quality image 64 (corresponding to a particular kernel 60) an iso-contour line 68 is identified for a constant match-quality. The constant match-quality may for example be a set based on an identification of the match-quality of a peak 70 of the surface 66, for example as defined by:

$$K = \rho_{max} - 0.04m \qquad (2)$$

where K is the constant match-quality of the iso-contour line; $\rho_{max}$ is the value of the quality match at the peak 70; and m is one standard deviation of quality match values.

At process block 72, a multi-dimensional model 74 may be fit to the iso-contour lines 68 where the multi-dimensional model 74 has generally the same dimensions as the reference data sets 32 and target data set 32′. Thus, for a two-dimensional data set, the multi-dimensional model will be an ellipse 76 having an aspect ratio as defined above representing a theoretical shape of a cross section through Gaussian correlation surface 66. This fitting process will yield a two-dimensionally located center-point 78 of the ellipse 76.

The matching process may, for example for a two-dimensional case, use the published algorithm described in A. W. Fitzgibbon, M. Pilu, and R. B. Fisher, "Direct Least Squares Fitting of Ellipses," in Proceedings of the 1996 International Conference on Pattern Recognition (ICPR '96) Volume I—Volume 7270: IEEE Computer Society, 1996 and hereby incorporated in its entirety by reference.

Alternatively, and referring momentarily to FIG. 3, for a three-dimensional reference data set 32 and target data set 32′, the model may be an ellipsoid 76′ fit to an ellipsoidal iso-contour surface 68′ to yield a three-dimensionally located center-point 78′ of the ellipsoid.

In both cases, a distance and direction between this center-point 78 and a center-point 80 derived from the first displacement image 50 defines a refinement vector 82 that when added to the vector 54 produces a corrected displacement vector 84.

This process of producing surfaces 66 and points 78 (78′) is repeated for the multiple kernels 60 as indicated by arrow 87 until corrected vectors 84 are produced for each such kernel 60 to provide a second displacement map 96 providing corrected displacement vector 84 per process block 88. It will be noted that the use of a multi-dimensional model 74 allows precision in the axial direction to augment precision in the non-axial direction providing improved axial and non-axial estimation accuracy.

The displacement map 86 may then be output as an elastographic or strain image per process block 90 by making certain assumptions about the stress field according to techniques well known in the art. The elastographic image may, for example, produce axial, lateral, and shear strains or other similar measures indicating elasticity, strain or local biomechanical environment.

It is specifically intended that the present invention not be limited to the embodiments and illustrations contained herein, but include modified forms of those embodiments including portions of the embodiments and combinations of elements of different embodiments as come within the scope of the following claims.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. These processors will generally implement "electronic computers" a term intended to an embrace not only conventional von Neumann architecture computers, but any electrical circuit capable of executing the algorithms described herein including, for example, digital signal processors (DSPs), field programmable gate arrays (FPGAs), application specific integrated circuits (ASICs) as well as other similar devices. Furthermore, references to memory, unless otherwise specified, can include one or more processor-readable and accessible memory elements and/or components that can be internal to the processor-controlled device, external to the processor-controlled device, and can be accessed via a wired or wireless network.

We claim:

1. An apparatus for obtaining elasticity images indicating elastic properties of a material subject to periodic compression comprising:
   an imaging apparatus for obtaining reference and target image information at different compressions, the image information having at least two spatial dimensions;
   an electronic computer executing a stored program and receiving the image information to:
   (a) compare corresponding portions of the reference and target image information to produce for each compared portion, match-quality information providing quantitative measures of a matching between the corresponding portions at multiple points each quantitative measure denoting different relative displacements in at least two spatial dimensions between the compared portions at which the matching occurs;
   (b) it a match-model having at least two spatial dimensions to the match-quality information for each compared portion;
   (c) extract a displacement value for at least one of the compared portions from a predetermined point of the fitted match-model; and
   (d) output human readable information indicating tissue elasticity based on multiple extracted displacement values of the predetermined points of the fitted match-model;
   wherein the match-model is a function derived from a point spread function of the imaging apparatus and represents expected matching in an elastic material; and
   wherein the match-quality information and the match-model have at least two spatial dimensions and wherein the match-model is fit to the match-quality information in at least two spatial dimensions identify single match center point as the predetermined point.

2. The apparatus of claim 1 wherein the match-quality information and the match-model have two spatial dimensions and wherein the match-model is an ellipse fit to a contour line of the match-quality information following a line of constant match-quality.

3. The apparatus of claim 2 wherein the constant match-quality is determined from a peak match-quality.

4. The apparatus of claim 2 wherein the imaging apparatus is an ultrasound machine collecting data along an axis by electronically manipulating received ultrasound echo signals along the axis and wherein the two spatial dimensions are one aligned with the axis and one perpendicular to the axis.

5. The apparatus of claim 1 wherein the image information and the match-model have three spatial dimensions and wherein the match-model is an ellipsoid fit to a contour surface of the match-quality information following a surface of constant match-quality.

6. The apparatus of claim 5 wherein the imaging apparatus is an ultrasound machine collecting data along an axis by a projection of ultrasound along the axis and wherein the three spatial dimensions are one aligned with the axis and two perpendicular to the axis and to each other.

7. The apparatus of claim 1 wherein the output is an image selected from the group consisting of a displacement, strain or displacement and strain related quantity.

8. The apparatus of claim 1 wherein the electronic computer selects portions of the reference and target image information for the comparison of (a) using pattern matching of portions of the reference and target image information.

9. The apparatus of claim 1 wherein the electronic computer up-samples the portions before the comparison of (a).

10. A method of obtaining elasticity images indicating elastic properties of a material subject to periodic compression comprising using an electronic computer executing a program stored in non-transient media to perform the steps of:
   (a) collecting reference and target image information at corresponding different compressions, the image information over at least two spatial dimensions having at least two spatial dimensions;
   (b) comparing corresponding portions of the reference and target image information to produce for each compared portion, match-quality information providing quantitative measures of a matching between the corresponding portions at multiple points each quantitative measure denoting different relative displacements in at least two spatial dimensions between the compared portions at which the matching occurs;
   (c) fitting a match-model having at least two spatial dimensions to the match-quality information for each compared portion;
   (d) extracting a displacement for each compared portion from a predetermined point of the fitted model the displacement indicating elastic properties of the material; and (e) outputting human readable information indicating tissue elasticity based on multiple extracted displacements of the predetermined points of the fitted match-model;
wherein the match-model is a function derived from a point spread function of the imaging apparatus and represents expected matching in an elastic material; and
wherein the match-quality information and the match-model have at least two spatial dimensions and wherein the match-model is fit to the match-quality information in at least two spatial dimensions identify a single match center point as the predetermined point.

11. The method of claim 10 wherein the image information and the match-model have two spatial dimensions and wherein the match-model is an ellipse fit to a contour line of the match-quality information following a line of constant matching.

12. The method of claim 11 wherein the ellipse has dimensions determined from an underlying resolution of an imaging apparatus collecting the reference and target image information in at least two dimensions.

13. The method of claim 11 wherein the reference and target image information is collected using an ultrasound machine collecting data along an axis by electronically manipulating received echo signal along the axis and wherein the two spatial dimensions are one aligned with the axis and one perpendicular to the axis.

14. The method of claim 10 wherein the image information and the match-model have three spatial dimensions and wherein the match-model is an ellipsoid fit to a contour surface of the match-quality information following a surface of constant matching.

15. The method of claim 14 wherein the reference and target image information is collected using an ultrasound machine collecting data along an axis along the direction of acoustic wave propagation and wherein the three spatial dimensions are one aligned with the axis and two to perpendicular to the axis and to each other.

16. The method of claim 10 wherein the output is an image selected from the group consisting of a displacement, strain and other quantity related to displacement or strain.

17. The method of claim 10 further including the step of computing displacements between the corresponding portions of the reference and target image information using pattern matching of sub-portions of the corresponding portions of the reference and target image information wherein the extracted displacement is based on a best matching of the sub-portions.

18. The method of claim 10 wherein the electronic computer up-samples the portions before the comparison of (b).

* * * * *

UNITED STATES PATENT AND TRADEMARK OFFICE
CERTIFICATE OF CORRECTION

PATENT NO. : 8,920,323 B2
APPLICATION NO. : 12/903748
DATED : December 30, 2014
INVENTOR(S) : Jingfeng Jiang et al.

It is certified that error appears in the above-identified patent and that said Letters Patent is hereby corrected as shown below:

IN THE CLAIMS

CLAIM 1, Col. 7, Line 62, delete "(b) it a match-model" and substitute therefore -- (b) fit a match-model --

Signed and Sealed this
Fourteenth Day of April, 2015

Michelle K. Lee
*Director of the United States Patent and Trademark Office*